United States Patent
Gray et al.

(10) Patent No.: US 10,413,702 B2
(45) Date of Patent: Sep. 17, 2019

(54) LOCKING CATHETER HUB

(71) Applicant: BOSTON SCIENTIFIC SCIMED, INC., Maple Grove, MN (US)

(72) Inventors: Jeff Gray, Sudbury, MA (US); Alison Lepordo, Methuen, MA (US); Nathan Zamarripa, Sudbury, MA (US); Karla Weaver, Framingham, MA (US); Thomas Pepin, Billerica, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 765 days.

(21) Appl. No.: 13/653,169

(22) Filed: Oct. 16, 2012

(65) Prior Publication Data

US 2013/0103004 A1 Apr. 25, 2013

Related U.S. Application Data

(60) Provisional application No. 61/550,167, filed on Oct. 21, 2011, provisional application No. 61/602,952, filed on Feb. 24, 2012.

(51) Int. Cl.
*A61M 27/00* (2006.01)
*A61M 25/00* (2006.01)
(Continued)

(52) U.S. Cl.
CPC ........ *A61M 25/0097* (2013.01); *A61M 25/04* (2013.01); *A61M 25/0074* (2013.01); *A61M 2025/0163* (2013.01)

(58) Field of Classification Search
CPC ............................................... A61M 25/0017
(Continued)

(56) References Cited

U.S. PATENT DOCUMENTS 2,185,741 A  1/1940  Sorg et al.
RE25,788 E   6/1965  Sheridan
(Continued)

FOREIGN PATENT DOCUMENTS

JP  S59-16119   1/1984
JP  S62-192174  8/1987
(Continued)

OTHER PUBLICATIONS

Golub et al., "Diffractive optical elements for biomedical applications", Conference Paper—Proceedings of SPIE, The International Society for Optical Engineering, vol. 3199, 1997, p. 220-231.
(Continued)

*Primary Examiner* — Tatyana Zalukaeva
*Assistant Examiner* — Guy K Townsend

(57) ABSTRACT

A drainage catheter, comprising an elongate body member, an elongate flexible member and a hub, the hub including a base and a collar, the base an internal passageway and a side lumen and an outer surface including an engagement element and a mating surface portion, and the collar including a side lumen extending from the inner surface to the outer surface and wherein the inner surface of the collar includes a mating surface portion and a counter element, wherein the elongate flexible member extends through the side lumen side lumens, and wherein the hub has an unlocked position where the engagement element and the counter element are not engaged and a locked position where the engagement element and the counter element are engaged, the collar is tightened on the base and the elongate flexible element is clamped between the mating surface portions of the base and the collar.

19 Claims, 9 Drawing Sheets

(51) Int. Cl.
*A61M 25/04* (2006.01)
*A61M 25/01* (2006.01)

(58) Field of Classification Search
USPC ............................................... 604/540
See application file for complete search history.

(56) References Cited

U.S. PATENT DOCUMENTS

| | | | |
|---|---|---|---|
| 3,318,335 A | 5/1967 | Heller | |
| 3,348,544 A | 10/1967 | Braun | |
| 3,470,869 A | 10/1969 | Fenton et al. | |
| 3,720,210 A | 3/1973 | Dietrich | |
| 3,725,522 A | 4/1973 | Sheridan et al. | |
| 3,752,510 A | 8/1973 | Windischman et al. | |
| 3,861,972 A | 1/1975 | Glover et al. | |
| 3,865,666 A | 2/1975 | Shoney | |
| 3,873,391 A | 3/1975 | Plauka et al. | |
| 3,914,002 A | 10/1975 | Berliner et al. | |
| 3,950,052 A | 4/1976 | Walter et al. | |
| 3,959,429 A | 5/1976 | Benning | |
| 3,985,601 A | 10/1976 | Panagrossi | |
| 3,989,571 A | 11/1976 | Harautuneian | |
| 4,085,185 A | 4/1978 | Adair | |
| 4,093,484 A | 6/1978 | Harrison et al. | |
| 4,154,244 A | 5/1979 | Becker et al. | |
| 4,171,943 A | 10/1979 | Tschanz et al. | |
| 4,191,185 A | 3/1980 | Lemieux | |
| 4,198,983 A | 4/1980 | Becker et al. | |
| 4,207,900 A | 6/1980 | Patel et al. | |
| 4,210,478 A | 7/1980 | Shoney | |
| 4,284,459 A | 8/1981 | Patel et al. | |
| 4,328,056 A | 5/1982 | Snooks | |
| 4,354,495 A | 10/1982 | Bodicky | |
| 4,489,961 A | 12/1984 | Laidig | |
| 4,509,877 A | 4/1985 | Sobin et al. | |
| 4,511,163 A | 4/1985 | Harris et al. | |
| 4,531,943 A | 7/1985 | Van Tassel et al. | |
| 4,557,781 A | 12/1985 | Hoppie | |
| 4,592,749 A | 6/1986 | Ebling et al. | |
| 4,596,563 A | 6/1986 | Pande | |
| 4,602,808 A | 7/1986 | Herron et al. | |
| 4,629,455 A | 12/1986 | Kanno | |
| 4,643,720 A | 2/1987 | Lanciano | |
| 4,655,762 A | 4/1987 | Rogers | |
| 4,737,219 A | 4/1988 | Taller et al. | |
| 4,753,765 A | 6/1988 | Pande | |
| 4,755,176 A | 7/1988 | Patel | |
| 4,778,550 A | 10/1988 | Barton et al. | |
| 4,802,947 A | 2/1989 | Bartholomew | |
| 4,806,182 A | 2/1989 | Rydell et al. | |
| 4,826,480 A | 5/1989 | Diaz et al. | |
| 4,838,269 A | 6/1989 | Robinson et al. | |
| 4,842,590 A | 6/1989 | Tanabe et al. | |
| 4,863,441 A | 9/1989 | Lindsay et al. | |
| 4,863,442 A | 9/1989 | DeMello et al. | |
| 4,874,373 A | 10/1989 | Luther et al. | |
| 4,875,481 A | 10/1989 | Higgins | |
| 4,886,506 A | 12/1989 | Lovgren et al. | |
| 4,950,257 A | 8/1990 | Hibbs et al. | |
| 4,959,067 A | 9/1990 | Muller | |
| 4,960,412 A | 10/1990 | Fink | |
| 5,035,686 A | 6/1991 | Crittenden et al. | |
| 5,037,403 A | 8/1991 | Garcia | |
| 5,041,095 A | 8/1991 | Littrell | |
| 5,085,645 A | 2/1992 | Purdy et al. | |
| 5,125,903 A | 6/1992 | McLaughlin et al. | |
| 5,125,913 A | 6/1992 | Quackenbush | |
| 5,129,887 A | 7/1992 | Euteneuer et al. | |
| 5,139,032 A | 8/1992 | Jahrmarkt et al. | |
| 5,143,409 A | 9/1992 | Lalikos | |
| 5,160,559 A | 11/1992 | Scovil et al. | |
| 5,167,647 A * | 12/1992 | Wijkamp ............ A61M 25/0043 604/532 |
| 5,181,750 A | 1/1993 | Reum | |
| 5,190,529 A | 3/1993 | McCrory et al. | |
| 5,201,723 A | 4/1993 | Quinn | |
| 5,217,555 A | 6/1993 | Franklin, III et al. | |
| 5,221,270 A | 6/1993 | Parker | |
| 5,226,898 A | 7/1993 | Gross | |
| 5,240,537 A | 8/1993 | Bodicky | |
| 5,248,305 A | 9/1993 | Zdrahala | |
| 5,254,107 A | 10/1993 | Soltesz | |
| 5,279,596 A | 1/1994 | Castaneda et al. | |
| 5,300,032 A | 4/1994 | Hibbs et al. | |
| 5,312,356 A | 5/1994 | Engelson et al. | |
| 5,318,032 A | 6/1994 | Lonsbury et al. | |
| 5,330,444 A | 7/1994 | Webler et al. | |
| 5,330,449 A | 7/1994 | Prichard et al. | |
| 5,344,412 A | 9/1994 | Wendell et al. | |
| 5,358,493 A | 10/1994 | Schweich, Jr. et al. | |
| 5,376,077 A | 12/1994 | Gomringer et al. | |
| 5,390,301 A | 2/1995 | Scherf | |
| 5,395,332 A | 3/1995 | Ressemann et al. | |
| 5,401,257 A * | 3/1995 | Chevalier, Jr. ...... A61M 25/0017 604/265 |
| 5,403,292 A | 4/1995 | Ju | |
| 5,419,764 A * | 5/1995 | Roll .................. A61M 25/0136 604/174 |
| 5,438,441 A | 8/1995 | Rockstroh et al. | |
| 5,466,230 A | 11/1995 | Davila | |
| 5,478,426 A | 12/1995 | Wiler et al. | |
| 5,507,728 A | 4/1996 | Erskine | |
| 5,514,112 A * | 5/1996 | Chu .................... A61M 27/00 604/265 |
| 5,533,988 A | 7/1996 | Dickerson et al. | |
| 5,539,175 A | 7/1996 | Smith et al. | |
| 5,545,151 A | 8/1996 | O'Connor et al. | |
| 5,557,652 A | 9/1996 | Henke | |
| 5,558,635 A | 9/1996 | Cannon | |
| 5,569,218 A | 10/1996 | Berg | |
| 5,695,467 A | 12/1997 | Miyata et al. | |
| 5,733,301 A | 3/1998 | Forman | |
| 5,762,637 A | 6/1998 | Berg et al. | |
| 5,772,642 A | 6/1998 | Ciamacco, Jr. et al. | |
| 5,803,510 A | 9/1998 | Dorsey, III | |
| 5,826,588 A | 10/1998 | Forman | |
| 5,830,401 A | 11/1998 | Prichard et al. | |
| 5,989,241 A * | 11/1999 | Plishka ............ A61M 25/0147 604/540 |
| 6,033,388 A | 3/2000 | Nordstrom et al. | |
| 6,074,379 A | 6/2000 | Prichard | |
| 6,165,152 A | 12/2000 | Becker et al. | |
| 6,177,648 B1 | 1/2001 | Lawson et al. | |
| 6,228,073 B1 | 5/2001 | Noone et al. | |
| 6,273,404 B1 | 8/2001 | Holman et al. | |
| 6,331,177 B1 | 12/2001 | Munnerlyn et al. | |
| 6,332,874 B1 | 12/2001 | Eliasen et al. | |
| 6,375,774 B1 | 4/2002 | Lunn et al. | |
| 6,454,740 B1 * | 9/2002 | Mody ............... A61M 25/0041 604/528 |
| 6,508,789 B1 | 1/2003 | Sinnott et al. | |
| 6,537,480 B1 | 3/2003 | Becker et al. | |
| 6,575,959 B1 | 6/2003 | Sarge et al. | |
| 6,618,174 B2 | 9/2003 | Parker et al. | |
| 6,648,874 B2 | 11/2003 | Parisi et al. | |
| 6,673,060 B1 * | 1/2004 | Fleming, III ......... A61M 1/008 600/149 |
| 6,696,667 B1 | 2/2004 | Flanagan | |
| 6,699,233 B2 * | 3/2004 | Slanda ................. A61M 25/00 604/523 |
| 6,858,104 B2 | 2/2005 | Flanagan | |
| 6,884,962 B2 | 4/2005 | Lizotte | |
| 7,128,737 B1 | 10/2006 | Goder et al. | |
| 7,201,763 B2 | 4/2007 | Heidner | |
| 7,217,256 B2 | 5/2007 | Di Palma | |
| 7,641,630 B2 * | 1/2010 | Accisano, III ...... A61M 25/007 600/585 |
| 7,740,608 B2 * | 6/2010 | Lampropoulos .. A61M 25/0097 604/523 |
| 7,824,367 B2 * | 11/2010 | Accisano, III .... A61M 25/0017 604/541 |
| 7,892,478 B2 | 2/2011 | Zhang et al. | |
| 7,951,206 B2 | 5/2011 | St. Pierre | |

(56) References Cited

U.S. PATENT DOCUMENTS

| | | | |
|---|---|---|---|
| 8,158,904 B2* | 4/2012 | Weber | B23K 26/073 |
| | | | 219/121.71 |
| 8,192,500 B2* | 6/2012 | Chung | A61F 2/04 |
| | | | 604/8 |
| 2001/0027310 A1 | 10/2001 | Parisi et al. | |
| 2001/0056273 A1* | 12/2001 | C | A61M 25/04 |
| | | | 604/509 |
| 2002/0039209 A1 | 4/2002 | Parker et al. | |
| 2003/0078613 A1 | 4/2003 | Heidner | |
| 2003/0120257 A1 | 6/2003 | Houston et al. | |
| 2003/0141002 A1 | 7/2003 | Flanagan | |
| 2003/0179452 A1 | 9/2003 | Lizotte | |
| 2004/0254562 A1 | 12/2004 | Tanghoj et al. | |
| 2005/0107739 A1* | 5/2005 | Palma | A61M 25/0097 |
| | | | 604/104 |
| 2005/0233025 A1 | 10/2005 | Zhang et al. | |
| 2006/0253104 A1* | 11/2006 | Pandey | A61M 27/008 |
| | | | 604/540 |
| 2007/0049906 A1* | 3/2007 | Magnusson | A61M 25/04 |
| | | | 604/540 |
| 2008/0125756 A1* | 5/2008 | Dicarlo | A61M 25/0097 |
| | | | 604/543 |
| 2009/0247990 A1 | 10/2009 | Ovcharchyn et al. | |
| 2011/0054447 A1* | 3/2011 | Johnson | A61M 1/008 |
| | | | 604/540 |
| 2011/0106059 A1* | 5/2011 | Graffam | A61M 25/0097 |
| | | | 604/544 |
| 2011/0125135 A1* | 5/2011 | Ahmed | A61M 25/04 |
| | | | 604/544 |
| 2011/0190734 A1 | 8/2011 | Graffam et al. | |
| 2011/0313403 A1* | 12/2011 | Hruska | A61M 25/0097 |
| | | | 604/540 |
| 2012/0184942 A1* | 7/2012 | Lareau | A61M 25/0102 |
| | | | 604/540 |
| 2013/0103004 A1* | 4/2013 | Gray | A61M 25/0097 |
| | | | 604/540 |
| 2014/0018778 A1* | 1/2014 | Lopera | A61M 27/00 |
| | | | 604/540 |
| 2014/0276655 A1* | 9/2014 | Murray | A61M 27/00 |
| | | | 604/540 |

FOREIGN PATENT DOCUMENTS

| | | |
|---|---|---|
| JP | 7241690 A | 9/1995 |
| JP | 8108287 A | 4/1996 |
| JP | 2003530116 | 10/2003 |
| WO | 9911315 A1 | 3/1999 |
| WO | 9920429 A1 | 4/1999 |
| WO | 0176677 A1 | 10/2001 |
| WO | 0177372 | 10/2001 |
| WO | 03002325 A2 | 1/2003 |
| WO | 2010062796 A1 | 6/2010 |

OTHER PUBLICATIONS

Lippert et al., Fundamentals and applications of polymers designed for laser ablation:, Applied Physics A, 2003, p. 259-264, vol. 77.

* cited by examiner

LOCKING CATHETER HUB

CROSS-REFERENCE TO RELATED APPLICATIONS

This application claims priority under 35 U.S.C. § 119 to U.S. Provisional Application Ser. No. 61/550,167, filed Oct. 21, 2011 and to U.S. Provisional Application Ser. No. 61/602,952 filed Feb. 24, 2012, the entirety of which are incorporated herein by reference.

FIELD OF THE INVENTION

This disclosure relates generally to catheters and more particularly to drainage catheters.

BACKGROUND

Typically, drainage catheters are tubular, flexible conduits percutaneously inserted into a fluid collection within the viscera. Common applications of drainage catheters include abscess, biliary, and nephrostomy drainage resulting from the body's temporary inability to naturally drain these fluid collections. A drainage catheter may be introduced over a stiffening cannula using either a direct trocar stick or a Seldinger technique, over a guidewire.

To inhibit catheter movement, a pigtail loop or other retention structure is often formed at the catheter's distal end. The loop, once formed, engages surrounding tissue, such as the inner walls of a lumen or organ, preventing the catheter from displacing due to accidental tugging or pulling.

Some catheters include a pre-formed pigtail loop at their distal end. Before placing this catheter in the body, a rigid wire is inserted to straighten out the loop. Once placed, the rigid wire is removed. Alternatively, the pigtail loop may be formed after the instrument is inserted at the desired location. In such catheters, a suture, fixed to the catheter's distal end, extends along the catheter's length, and exits from its proximal end. By drawing the suture proximally, the distal tip of the catheter is forced to curl into a pigtail formation. A proximal suture portion is then secured to hold it in place and retain the loop shape at the distal end of the catheter.

Many such lockable pigtail loop catheters are available today. Some lockable catheters include a locking mechanism that requires a separate unlocking tool. If the unlocking tool is misplaced, it may be difficult to release such sutures and disengage the catheters. Other lockable catheters do not require external unlocking tools, rendering them susceptible to being inadvertently unlocked.

Therefore, there remains room for improvement and/or alternatives in providing tamper-resistant structures for drainage catheters.

SUMMARY

Embodiments of the present disclosure pertain to drainage catheters, as well as related components, systems and methods. Some embodiments provide for alternative structures, methods of making, and methods of using drainage catheters. In many instances, it may be desirable to fix drainage catheters within a patient's body to drain fluid. Pigtail loops or other retention structures such as malecot elements may be formed at the distal end of these catheters to prevent displacement. Some embodiments of the present disclosure introduce a novel locking hub to secure a suture thread or the like for holding the pigtail loop in place. The locking hub may have a simple construction and is easy use.

In some embodiments, the drainage catheter includes an elongate body member, an elongate flexible member, and a hub coupled to the elongate body member. The elongate body member includes a central lumen, and at least a portion of the elongate body member is placed within a patient. The elongate flexible member is operably coupled to the elongate body member and it extends through the lumen of the elongate body member. The hub further includes a base and a collar. The base has a central lumen, an outer surface, and a side lumen extending from the central lumen to an opening in the outer surface. The outer surface of the base further includes a screw thread and a mating surface portion. The collar has a central lumen, an inner surface, and an outer surface. A screw thread is disposed on the inner surface and configured to mate with the screw thread of the base. The collar's inner surface further includes a mating surface portion. The mating surfaces of the base and the collar may have mismatched profiles and they may be configured such that when the collar is tightened on the hub using the corresponding screw threads, the mating surfaces are forced together to lock the collar to the base. The collar may also include a side lumen extending between the inner surface and the outer surface. The elongate flexible member may extend through the base side lumen and the collar side lumen.

In some embodiments, the hub further includes a soft outer jacket slidable over the base and the collar. The outer jacket may have a cavity for receiving the base and the collar through a proximal opening. In one embodiment, the soft outer jacket further comprises a distal portion that tapers and extends distally beyond the distal ends of the base and the collar.

In some embodiments, the base mating surface includes a tapered surface that tapers at a first angle and the collar mating surface includes a tapered surface that tapers at a second angle. The first and second angles are different, and in some embodiments, the second angle is greater than the first.

In some embodiments, the base mating surface is distal of the screw thread disposed on the base outer surface and the collar mating surface is distal of the screw thread disposed on the collar inner surface. Moreover, the collar mating surface may be proximal the collar side lumen.

In some embodiments, the elongate flexible member has a first end fixed to the hub, a second end portion extending through the base side lumen and the collar side lumen, and a middle portion distal of the first end and the second end portion that is operably connected to the distal portion of the elongate body member.

In some embodiments, relative proximal movement of the elongate flexible member and the hub causes the distal portion of the elongate body member to change shape. For example, the proximal movement of the elongate flexible member and the hub may cause the distal portion of the elongate body member to form a loop such as a pigtail loop or the like.

In some embodiments, tightening of the collar to the base reduces and/or prevents relative movement between the elongate flexible member and the hub. To this end, a portion of the elongate flexible member is fixed between the collar and the base.

In some embodiments, a resilient seal is disposed in the base side lumen. The resilient seal, which substantially prevents fluid flow through the side lumen, may be composed of silicone.

In some embodiments, a locking member is included between the base and the collar. The locking member may be a spring and may fixed to one of the base and collar or may be trapped between the base and the collar. The locking member may, for example, be placed in a slit provided for the purpose in the base. A locking cavity may be provided in the collar to receive a portion of the locking member when the collar is locked to the base to provide further positive retention of the collar on the base. The locking member may be released from its position within the locking cavity to allow the collar to release from the base. This release may be effected by pressing down on the locking member to move it from the locking cavity. A second locking cavity in the collar may be provided to retain the collar and base in relative position prior to the collar being tightened on the base. The locking member may be retained between the collar and the base in a partially compressed position even when the collar is not locked to the base. This may help prevent the collar from shifting with respect to the base.

The present disclosure further describes methods for locking a catheter in a patient. In some embodiments, the method includes the steps of providing a drainage catheter, and inserting at least a portion of the drainage catheter into the patient. The method may further include pulling an elongate flexible member proximally through side lumens in the base and the collar to form a loop such as a pigtail loop in a distal portion of the elongate body member, and locking the collar to the base and thereby temporarily or permanently fixing a portion of the elongate flexible member between the collar and the base. The method may further include the step of pulling a jacket proximally over the collar and the base to cover the collar and a distal portion of the base.

The foregoing and other objects, aspects, features, and advantages of the present disclosure will become apparent from the following description, the drawings, and from the claims.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF SELECTED EMBODIMENTS

Figure 1A:
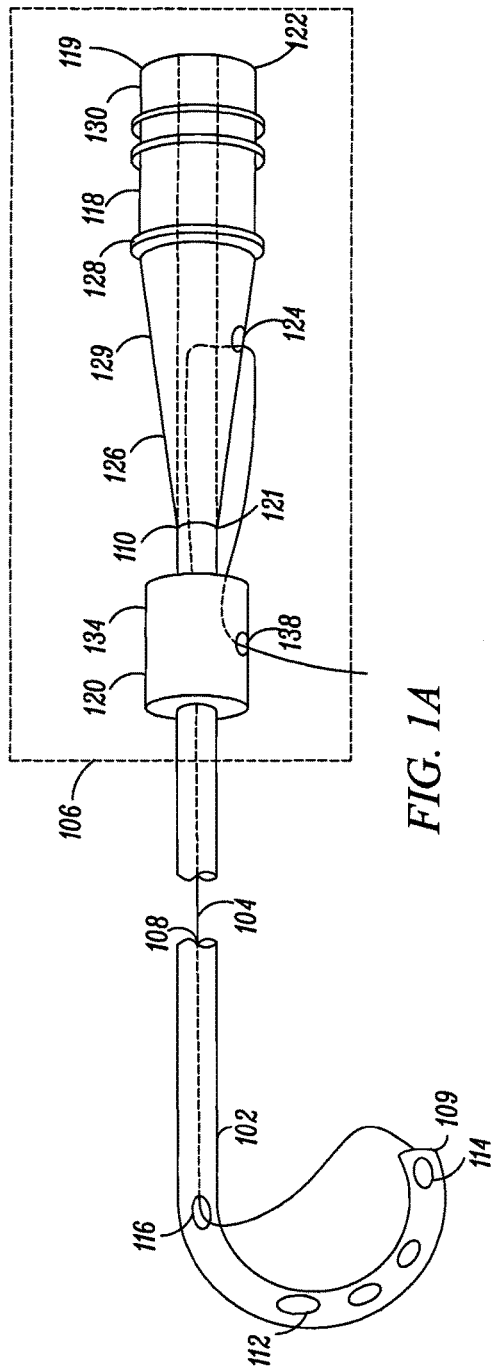
FIG. 1A is an illustrative diagram of a drainage catheter according to one embodiment of the present disclosure.

Reference will now be made in detail to some example embodiments of the present disclosure, an example of which is illustrated in the accompanying drawings. Wherever possible, the same reference numbers will be used throughout the drawings to refer to the same or like parts.

For purposes of this disclosure, "proximal" refers to the end closer to the device operator during use, and "distal" refers to the end further from the device operator during use.

Overview

Embodiments of the present disclosure introduce drainage catheters used to drain viscera such as the kidneys, bladder, abdominal cavity, stomach, and biliary system. These catheters may include a retention element such as a pigtail loop with a novel suture-locking hub. The locking hub minimizes tampering risks by providing a retention system, which is difficult to inadvertently open, yet does not require any additional unlocking tools. The locking hub may include a base attached to the proximal end of the catheter. A flexible member such as a suture may be connected to the distal end of the elongate member and may extend through the elongate member towards the hub. In the hub, the suture may exit from a small opening in the base. Proximally pulling the suture thread may actuate the retention element forming the pigtail loop. A collar may cover the base, retaining the suture between the collar's inner surface and the base's outer surface. A screw-fit lock including a screw threading on the outer surface of the base may engage a corresponding screw thread on the inner surface of the collar to lock the base and the collar. The base's outer surface and the collar's inner surface may also positively engage when the screw threads are engaged to provide further retention. The base may taper distally at a particular angle, while the collar may taper at a different angle. Moreover, the collar may taper at a sharper angle than the base making the tapered collar diameter slightly lesser than the corresponding diameter of the base.

The following exemplary embodiments illustrate the retention element as a pigtail loop. It will be understood, however, that this depiction is merely exemplary and not meant to limit the scope of the present disclosure. For example, the retention element may be a malecot element, an element having struts or any other element that can be expanded, contracted or otherwise actuated to change configuration to secure the catheter within a patient.

Exemplary Embodiments

FIG. 1 illustrates an exemplary drainage catheter including an elongated body member 102, an elongate flexible member 104 (or flexible member 104), and a hub 106.

The elongated body member 102 includes a central lumen 108 extending from its distal end 109 to its proximal end 110. The member 102 may have any cross-sectional shape, such as circular, rhombic, rectangular, oval, semicircular, or any other suitable shape. Moreover, the elongated member diameter may vary depending on the quantity of fluid to be extracted, fluid density, the size of the body cavity or cannula used to guide the elongated member 102 towards the desired location. Further, the elongated body member 102 may have a uniform cross-section or diameter from its distal 109 to proximal end 110. Alternatively, the cross-section and diameter may vary through its length.

The elongated body member's distal portion includes one or more apertures 112 to facilitate fluid flow from the patient's body to the central lumen 108. These apertures can be adapted to fit the needs of a given application. For example, the number of apertures 112 and their shape may vary based on the nature of the fluid. For example, if the fluid is viscous, the apertures 112 may be larger or more numerous. Alternatively, if the fluid has lower density, the apertures 112 may be smaller or lesser in number. It will be understood that the size and number of apertures are not restrictive, and elongated members with any size and number of apertures are well within the scope of the present disclosure.

Because the elongated body member 102 is within a patient's body for short or extended periods, the device is made of non-allergic or biocompatible material. Such materials include, for example, silicones and polyurethanes. It will be understood that any other suitable material may just as easily be used. In one embodiment, the elongated member 102 may be coated with an anti-bacterial coating to inhibit bacterial growth on its surface. The anti-biotic coating may contain an inorganic anti-biotic agent, disposed in a polymeric matrix that adheres the anti-biotic agent to the elongate member's surface. Further, a drug releasing coating may also be applied to the outer surface of the elongated member 102, assisting in healing. In another embodiment, the elongated member 102 includes a lubricious coating to facilitate convenient insertion.

The flexible member 104 may be coupled to a distal portion of the elongated body member 102, and it may exit the elongated body member 102 through a distal opening 114. From here, the elongated flexible 104 member may reenter the central lumen 108 through a second opening 116 disposed at a little distance from the distal end 109. Within the central lumen 108, the flexible member 104 travels from the distal end to the proximal end, and then extends out of the elongated member 102. This member may be a suture thread made of nylon or other similar material of comparable strength. Alternatively, the member may be a thread or a flexible metal wire.

In another embodiment, instead of attaching to the distal end 109 of the elongated member 102, the flexible member 104 may be coupled to the elongate member-hub junction. From this junction, this member extends distally through the central lumen 108 towards the distal end 109. From there, it exits the lumen 108 through the distal opening 114 and reenters the lumen from the second opening 116. It then returns proximally through the central lumen 108 towards the hub 106. To attach the flexible member 104 to the elongate member's distal end 109 or the elongate member-hub junction, suitable coupling techniques, such as tying, gluing, or piercing, may be used.

The hub 106 includes a base 118 and a collar 120. The base 118 is a cylindrical tube including a proximal end 119, a distal end 121, an internal passageway 122, a side lumen 124, and an external surface 126. Its distal end 121 is coupled to the elongated body member's proximal end 110, and its internal passageway 122 (extending along its length) is coaxial with the central lumen 108. The external surface 126 of the base 118 tapers from its proximal end 119 to its distal end 121, and it includes an engagement element 128. In one embodiment, only a portion of the base 118 tapers. In this case, the tapering may begin distal of the engagement element 128 and extend to the distal end 121. The side lumen 124 extends from the internal passageway 122 to the external surface 126. This lumen provides a path for the flexible member 104 to exit the base 118.

A mating surface 129 is present on the external surface 126. This portion may begin distal of the engagement element 128 and extend up to the base's distal end 121. Alternatively, the mating surface 129 may extend for a portion of the external surface 126 distal of the engagement element 128. In one embodiment, the mating surface 129 tapers proximally to distally.

In addition to the elements described in the immediately preceding section, the base 118 may further include screw threads 130 at its proximal end 119. These screw threads 130 attach peripheral instruments to the drainage catheter 100 such as collection bags, drainage tubes, syringes, and so on. It will be understood that instead of the threaded arrangement, other means may also be employed to attach peripheral equipment to the hub 106. For example, snap fit arrangement may be employed.

Base 118 may be composed of a semi-rigid material such as molded biocompatible plastic, nylon, polyethylene, ethylene-vinyl acetate co-polymer, or a shape memory metal, such as nitinol. Alternately, a semi-rigid compliant member, such as rubber may form the base 118.

Figure 1B:
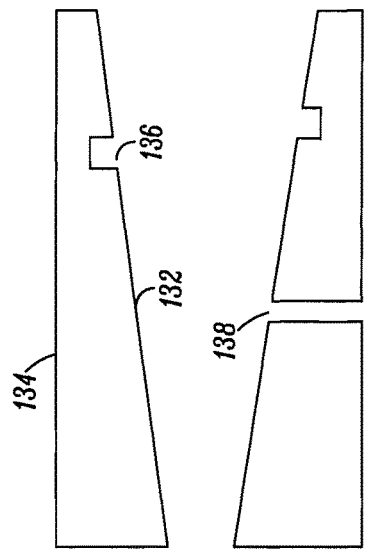
FIG. 1B is a cross-sectional view of an exemplary collar according to one embodiment of the present disclosure.

Collar 120 is a hollow cylindrical structure that snuggly fits around the base 118 when the distal end 109 is placed at the desired location within a patient's body. FIG. 1B is a cross-sectional view of the collar 120. It includes a tapered inner surface 132, mating surface 133, and an outer surface 134. Moreover, like the external surface 126 of the base 118, the collar's inner surface 132 may also taper from its proximal end to its distal end, as illustrated, or vice versa. The tapering angle, however, differs from the base's tapering angle. In one embodiment, the collar's tapering angle is greater than that of the base 118. Further, the collar's inner surface 132 includes a counter element 136 that may mate with the engagement element 128 when the collar 120 is placed around the base 118. The collar 120 also includes a side lumen 138 that extends from the inner surface 132 to the outer surface 134. The flexible member 104 may pass through this side lumen 138. The mating surface 133 extends from the counter element 136 to the collar's distal end. Alternatively, the mating surface 133 may begin distal of the counter element 136 and its length may be equal to the length of the base's mating surface 129.

Engagement element 128 and counter element 136 are shown as a helical male thread and a corresponding female thread. These threads may be mating threads or they may have slightly different pitches so that the force between the threads may add to the force between the collar 120 and the base 118 when locked together. The structure of the engagement element 128 and the counter element 136 may vary in different embodiments of the drainage catheter 100. For example, these elements may be helical male and female threads, members of a snap-fit assembly, male and female luer-lock elements, protrusions and notches, ratcheting members, etc. It will be understood that any suitable engagement element 128 and counter element 136 may be utilized without departing from the scope of the present disclosure.

Similar to the base, the collar 120 may also be formed of a semi-rigid or rigid material, such as nylon, rubber, biocompatible plastic and so on.

Figure 2A:
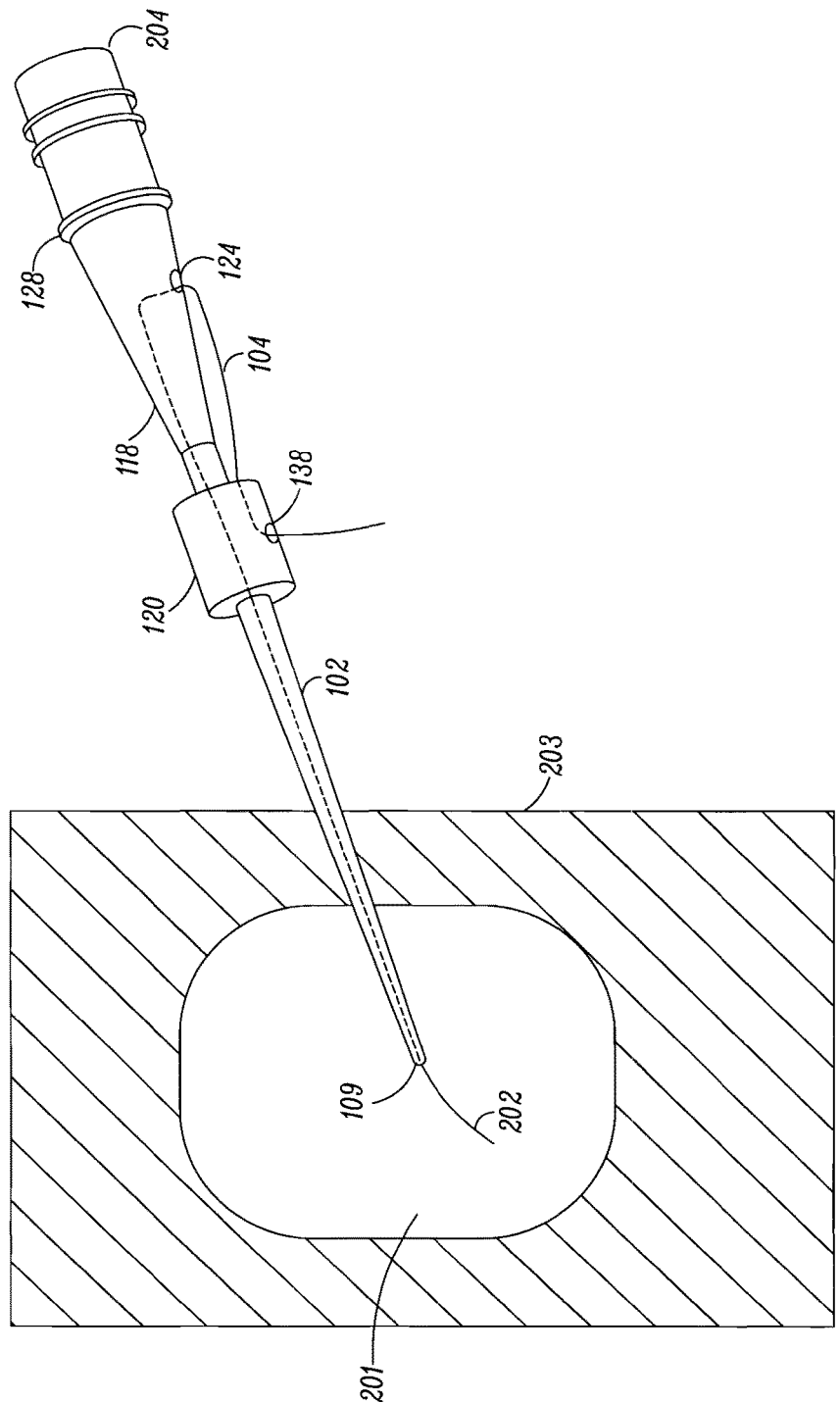
FIG. 2A is an illustrative diagram of the drainage catheter disposed within a patient in an unlocked position according to one embodiment of the present disclosure.
Figure 2B:
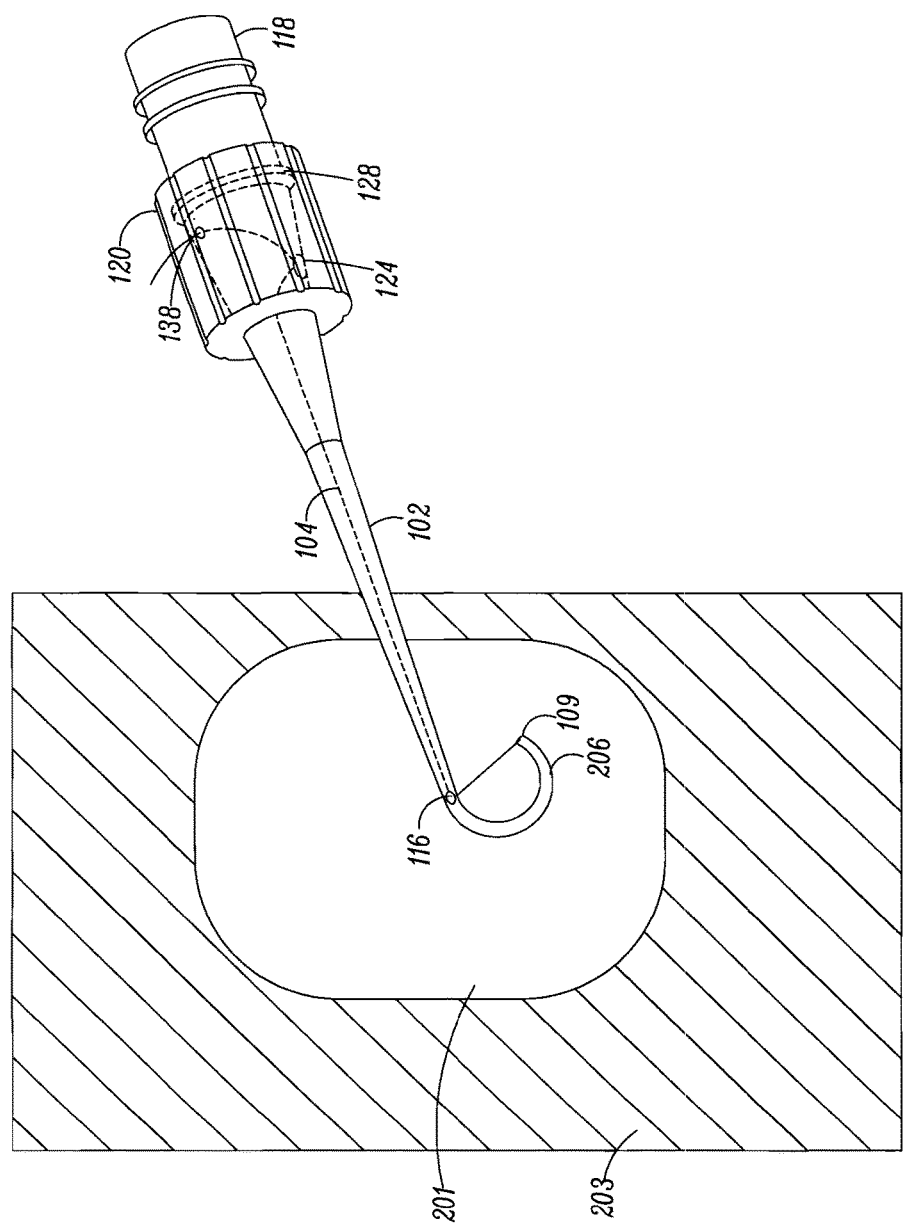
FIG. 2B is an illustrative diagram of the drainage catheter disposed within a patient in a locked position according to one embodiment of the present disclosure.

The structural features of the drainage catheter 100 are described with reference to FIG. 1A and FIG. 1B. The following figures (FIGS. 2A and 2B) describe the catheter's functional features, including a method of locking the flexible member 104 in the hub 106. FIG. 2A illustrates the drainage catheter 100 in a first position, with hub 106 in an unlocked state; and FIG. 2B illustrates the drainage catheter 100 in a second position, with hub 106 in a locked state. The figures, in succession, illustrate a process of inserting the drainage catheter 100 in a patient's body, forming a pigtail loop, and securing the flexible member 104 to maintain the pigtail loop.

Initially, to insert the distal end 109 within a cavity 201 in the patient's body 203, the elongated member 102 is straightened with a stiffening stylus 202 disposed within its central lumen 108. A guide wire is also inserted in the central lumen 108 to guide the catheter to the desired location. The straightened elongated member 102 is then advanced to the cavity 201 using any suitable procedure such as percutaneous insertion, or insertion through a body cavity. Once in place, the guide wire and stiffening stylus 202 are withdrawn by pulling them back out of the catheter's proximal end 204.

During this insertion procedure, the collar 120 is not secured over the base 118. It may instead rest around the proximal portion of the elongated member 102. Moreover, the flexible member 104 extends from the elongated member 102 to the base 118. From the base 118, the flexible member 104 exits via the side lumen 124, enters the collar 120, and exits the collar 120 through the collar's side lumen 138. A portion of the flexible member extends out from the collar's side lumen 138.

Once the catheter is in place, a pigtail loop is formed and secured. This operation is illustrated in FIG. 2B. An operator may pull the flexible member 104 extending from the side lumen 138 to draw the distal end 109 of the elongated member 102 proximally, forcing it to curl up and form the pigtail loop 206. To lock the pigtail loop 206, the operator, while pulling the flexible member 104 taut with one hand, may move the collar 120 towards the base 118 with the other hand. The collar 120 is pushed until the collar's counter element 136 contacts the engagement element 128.

In one embodiment, the engagement element 128 and the counter element 136 are helical external and internal screw threads, respectively. Once contacted, the collar 120 may be twisted, to engage the external screw thread in the internal thread, locking the base 118 and the collar 120. Further, the helical external and internal screw threads may extend less than 360° around the base's external surface, and their major diameter may be lesser than their lead.

The collar length and its taper angle may be selected such that when the screw thread of the collar 120 reaches the helical screw thread on the base 118, the inner diameter of the distal end of the collar 120 is equivalent to the outer diameter of the base portion that is in contact with the collar's distal end. So, when the collar 120 is screwed on the base 118, the collar 120 twists proximally, forcing the mating surface 133 of the collar 120 into a tight fit over the mating surface 129 of the base 118 and sealing the space between collar 120 and base 118. This mechanism introduces a double lock. Because of the force exerted by the tight fit between the mating surfaces of the base 118 and collar 120, it is difficult to disengage the hub 106. Moreover, even if the engagement element 128 wears off over time, or is inadvertently disengaged, considerable force is required to separate the collar 120 and the base 118 because of the mating force between their mating surfaces. Therefore, the pigtail loop 206 stays intact even if the device is tampered with.

Figure 3:
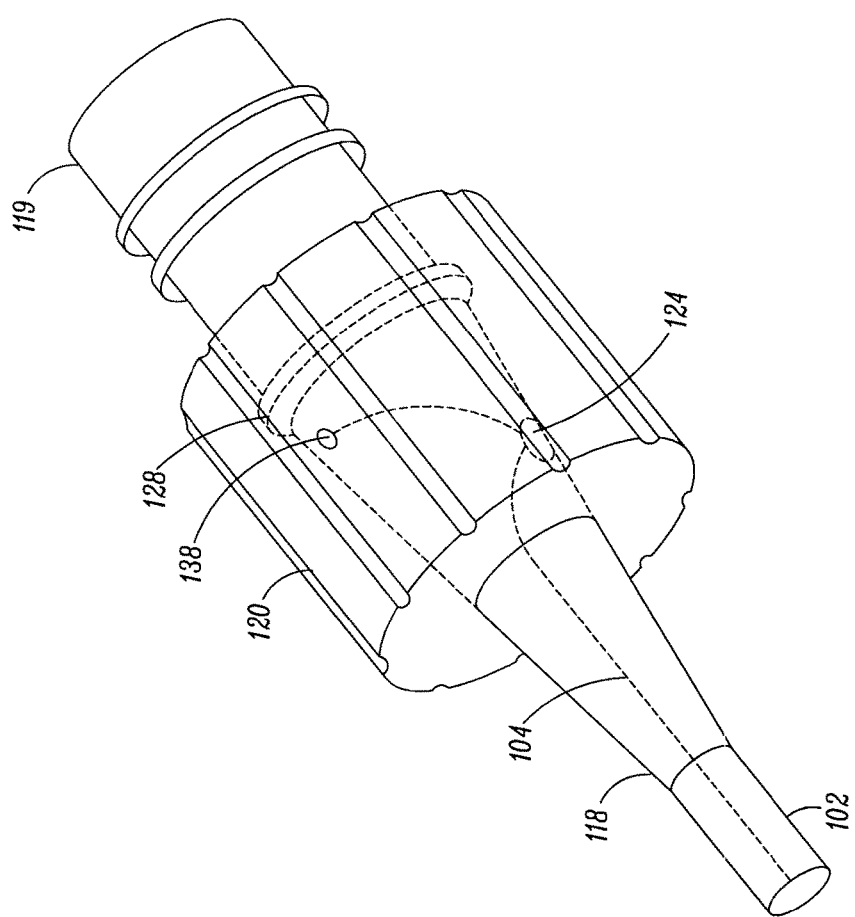
FIG. 3 illustrates components of a drainage catheter hub in a locked position.

FIG. 3 is a detail view of hub 106 in the locked position. Here, a portion of the flexible member 104 (between the side lumen 124 and the side lumen 138) is trapped between the collar 120 and base 118, preventing any movement. It will be understood that once locked, the side lumens should not overlap one another. The separation between the two lumens 124, 138 determines the length of flexible member 104 trapped between the base 118 and the collar 120. To reduce the strain on the flexible member 104, it is advisable to have a relatively lengthy portion between the lumens. Therefore, the lumens may be placed as far away from each other as possible.

In the locking position, side lumens 124 and 138 may be in a variety of relative positions. For example, the lumens may lie in the same longitudinal plane, but be circumferentially separated from one another. A second example position occurs with the lumens lying in the same circumferential plane, but in different longitudinal planes. In another exemplary embodiment, the lumens could lie in different circumferential and longitudinal planes along the surface of the base 118 and the collar 120. The side lumens 124, 138 may be positioned anywhere along the external surface of the base 118 and collar 120.

It will be understood that the helical screw thread assembly illustrated in the figures is merely exemplary. The engagement element 128 and counter element may be any suitable engaging arrangement without departing from the scope of the present disclosure. For example, the engagement and counter elements may be elements of a snap fit assembly or a luer-lok assembly. Alternatively, the engagement element 128 may be multiple spring-loaded angular projecting flanges while the counter element may carry similarly shaped grooves. When the collar 120 travels proximally over the base 118 the projections may engage the grooves locking the collar 120 to the base 118. To unlock the hub 106, the base 118 may include a spring-release button. Pressing this button contracts the spring in the flanges, pulling the flanges towards the base's surface, thereby releasing them from the groove, and unlocking the hub 106. To ensure that the release button is not accidentally pressed, it may be embedded in the base's body between the inner and out surface, similar to reset buttons present on most electronic devices. Any other suitable engagement mechanism may be contemplated and is within the scope of the present disclosure.

To complete placement, the excess flexible member 104 extending from the collar's side lumen 138 is trimmed. With the flexible member 104 trimmed, if the catheter 100 is accidentally unlocked, the pigtail loop 206 at the distal end may straighten out, and the proximal end of the flexible member 104 may be lost within the central lumen 108. It can be difficult to extract the flexible member 104 in this situation. To overcome this difficulty, the proximal portion of the flexible member 104 may be coiled around the base 118 before the collar 120 is locked in place and the flexible member 104 is trimmed. This excess flexible member 104 between the base 118 and the collar 120 allows operators to unlock the hub 106, straighten the pigtail loop 206, and manipulate the placement of the elongated member 102 without losing the flexible member 104.

Figure 4:
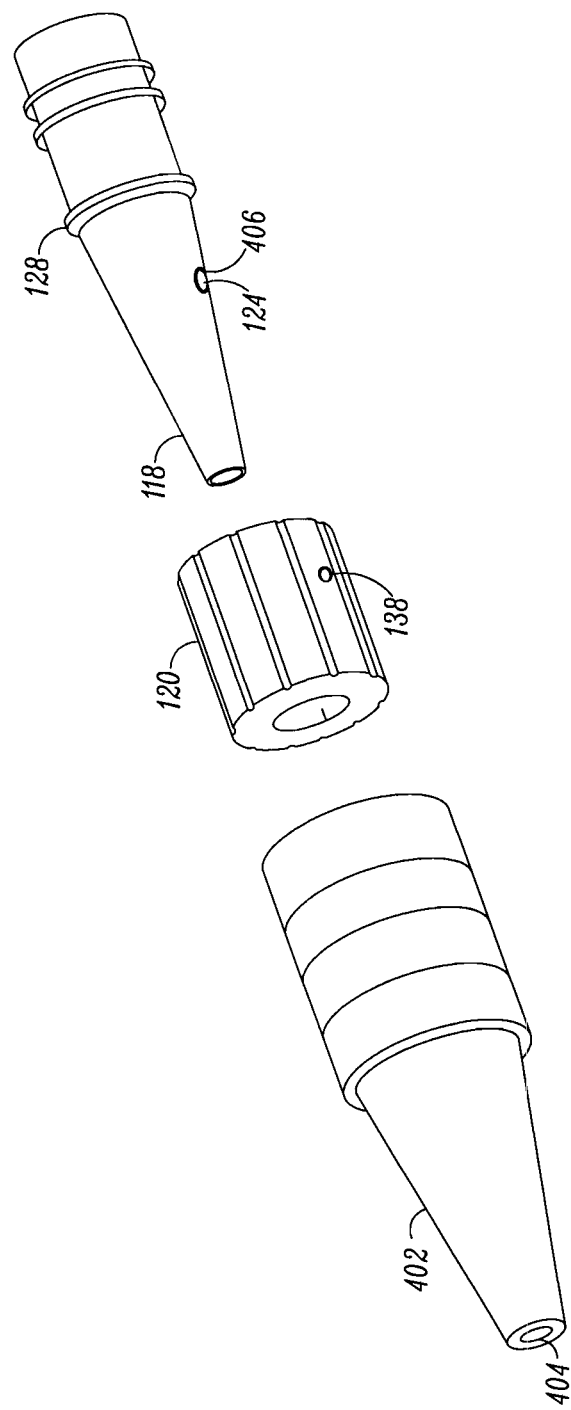
FIG. 4 is an exploded view of drainage catheter hub components.

It will be understood that various alternatives may be contemplated for the hub 106. FIG. 4 illustrates one such alternative. Here, the hub 106 includes a jacket 402 that covers both the base 118 and the collar 120, in an assembled condition. In one embodiment, the jacket 402 may be made of a pliable material that deforms under pressure or that may change its shape according to underlying instruments. Such material may include rubber, polymer, nylon, etc. A flexible jacket 402 may be used because the external surface of the hub 106 is uneven, and fitting a rigid jacket over this surface may pose difficulties.

Further, the jacket 402 includes a cavity 404 coaxial with the base's internal passageway 122. The jacket 402 is pulled proximally over the collar 120 and base 118, to prevent accidental tampering. In the illustrated embodiment, the jacket 402 tapers distally and extends beyond the distal ends of the base 118 and the collar 120. Alternatively, a distal portion of the jacket 402 could taper, while its proximal portion maintains a uniform cross-section.

In another embodiment, the jacket 402 may be made of two equal and identical shaped portions, obtained by, for example, slicing the jacket longitudinally. These longitudinal portions align to form the jacket. In an embodiment, the two longitudinal portions may cover the collar and base such that the two ends of the longitudinal portion touch each other. Subsequently, the portions may be secured using known securing mechanisms such as snap-fitting, locking, glue, etc. Alternatively, the two portions may be hingedly attached from one end, while the other end may swing open. In this implementation, when the two free ends contact each other, they form a hollow space within to cover the hub. The jacket may open around the hinge to place over the collar and base. Once placed, the jacket 402 may be closed, and suitable mechanisms may be included to lock the open edges of the jacket 402. In these embodiments, the internal surface of the jacket 402 may be shaped like the external hub surface. As the jacket 402 opens laterally, it can easily fit over the hub 106, and, therefore, it may not be made of a flexible or elastic material. Instead, the jacket 402 may be formed of any suitable rigid or semi-rigid material, such as plastic, metal, polymer, and so on.

As illustrated in FIG. 4, the base's side lumen 124 is distal of the engagement element 128. This placement minimizes potential interference between the flexible member 104 and any peripheral instruments attached to the proximal end of the hub 106. Placing the side lumen 124 distal of the engagement element 128, however, may result in fluid leakage through that lumen. To prevent such leakage, the side lumen 124 may include a sealing member 406. Any sealing member, such as a pliant plug having a threadable hole may be used. Likewise, insoluble materials with self-sealing properties may seal the lumen. Such materials include silicone, wax, rubber, or latex. In some embodiments, the collar's side lumen 138 may also be sealed in a similar manner. Alternatively, a deformable sealing material may be disposed between the base 118 and the collar 120, providing a similar sealing function when locked together.

Figure 5:
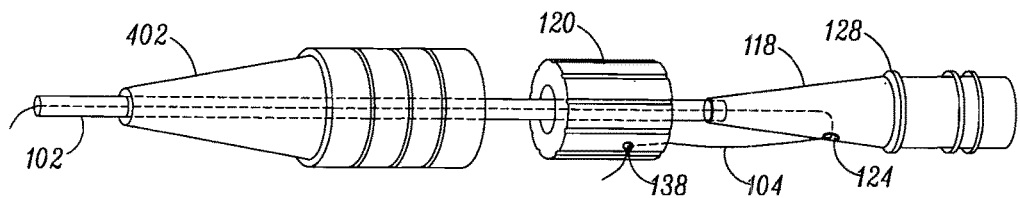
FIG. 5 is an illustrative diagram of a hub assembly of the drainage catheter according to one embodiment of the present disclosure.

FIG. 5 is a detail view of the hub 106 of FIG. 1 with the jacket 402. Here, the jacket 402 lies on the proximal portion of the elongated member 102 distal of the collar 120 and base 118. When the hub 106 is assembled for locking, the collar 120 engages with the base 118 and locks the flexible member 104 in position. The jacket 402 then slips over the locked base and collar assembly, isolating it from external conditions.

Figure 6:
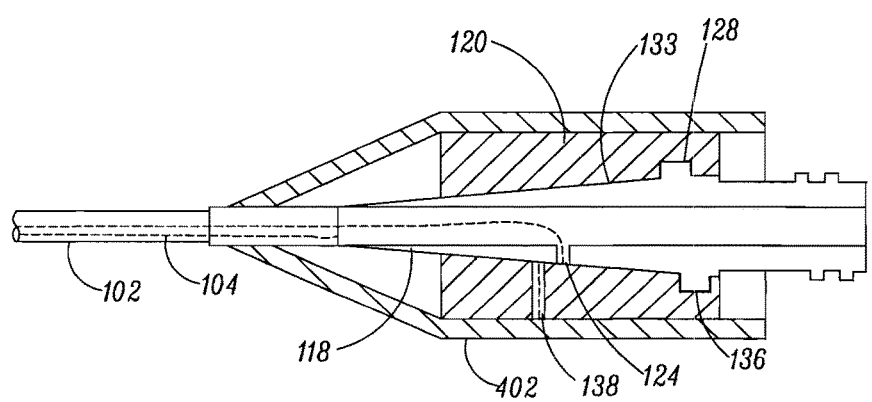
FIG. 6 is an illustrative diagram of the hub assembly of FIG. 4 with a jacket according to one embodiment of the present disclosure.

FIG. 6 is a sectional view of the hub 106 and the jacket 402 in the locked state. The internal lumens, passageways, and surfaces of the elongated member 102, base 118, collar 120, and jacket 402 are visible in this view. The proximal diameter of the elongated member 102 is sized to match the distal diameter of the base 118, providing a smooth transition from one lumen to the other. For instance, the elongated member 102 and the base 118 may be fused or bonded to one another. The internal passageway 122 may gradually increase in diameter from the distal end 121 to the proximal end 119. Alternatively, the passageway 122 may remain uniform throughout the length of the base 118, or it may taper towards the proximal end, neither case departing from the scope of the present disclosure.

FIG. 6 illustrates the inner surface 132 of the collar 120 along with the mating surface 133, the counter element 136, and the side lumen 138. The inner surface 132 of the collar 120 tapers from the proximal end to the distal end or vice versa. As described previously, the collar's taper angle may differ from that of the base 118. For example, the tapering angle of the collar's inner surface 132 may be greater than the tapering angle of the base's outer surface 126. Because the tapering angle is greater, the collar's mating surface 133 tightly fits around the base's mating surface 129 providing an airtight surface lock between the collar 120 and base 118.

The internal surface of the jacket 402, as depicted, follows the contour of the collar 120 up to the distal end of the collar 120. From there on, the jacket 402 tapers at a suitable angle towards the elongated member 102. The tapering angle determines the length of the jacket 402 distal of the collar 120; the sharper the angle, the shorter the jacket 402.

FIG. 6 also illustrates the embodiment where the flexible member 104 is attached to the junction between the elongated member 102 and the base 118. Here, the flexible member 104 travels distally through the central lumen 108 towards the distal end 109, threads between the distal opening 114 and second opening 116, and returns through the central lumen 108 toward the hub 106. In the hub 106, the flexible member 104 exits from the side lumens of both the base 118 and the collar 120.

Figure 7:
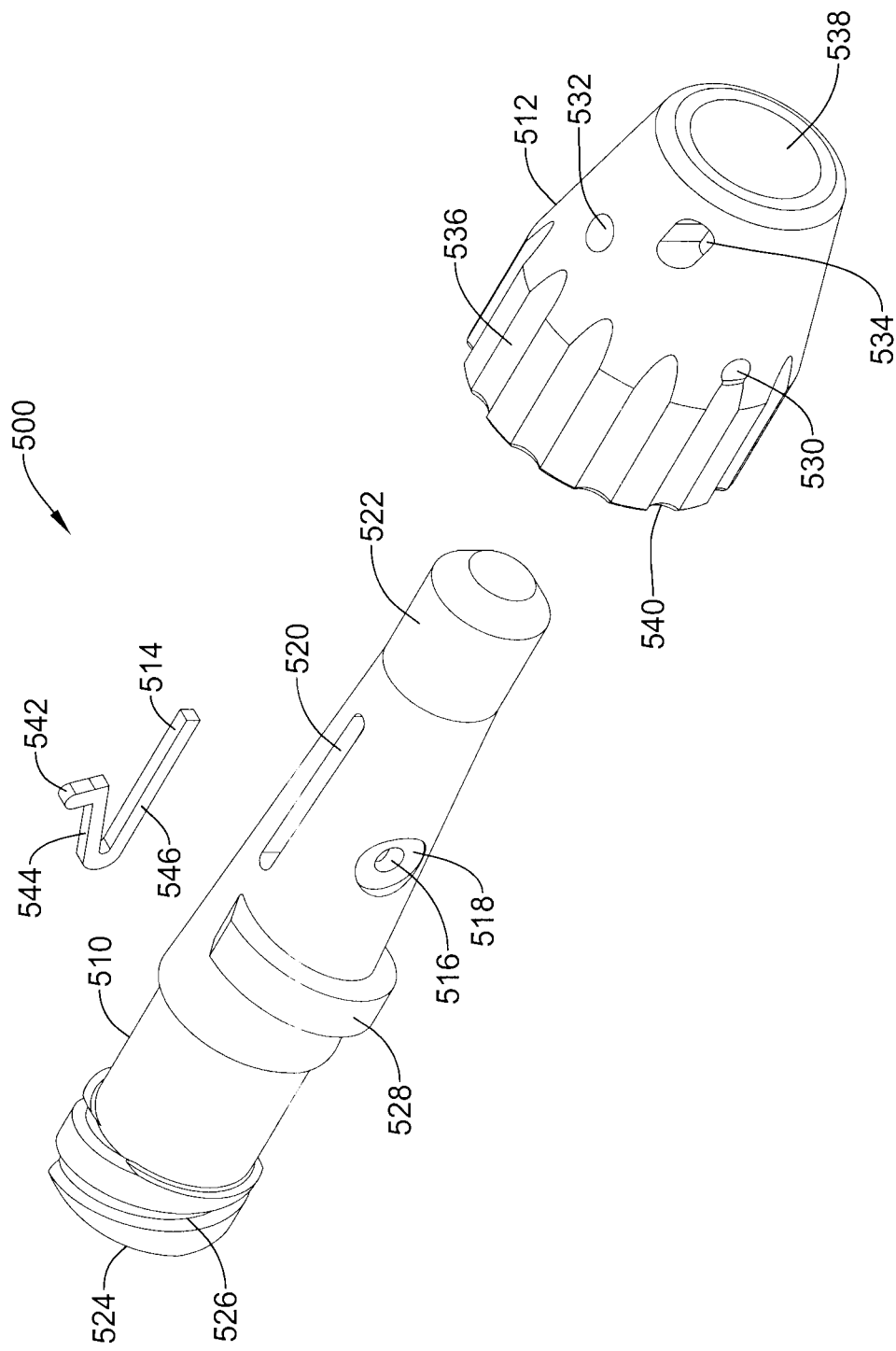
FIG. 7 is an exploded view of drainage catheter hub components.
Figure 8:
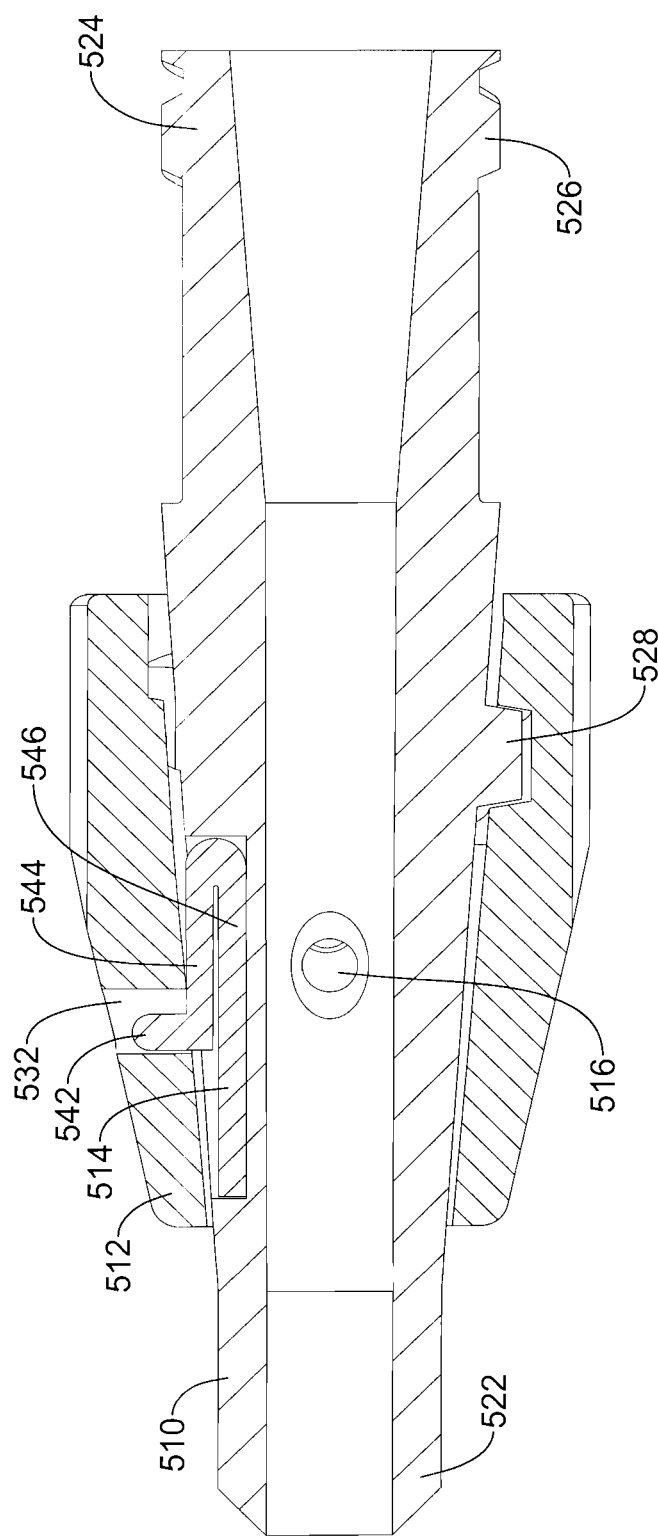
FIG. 8 is a cross sectional view of the drainage catheter hub of FIG. 7 in a locked position.
Figure 9:
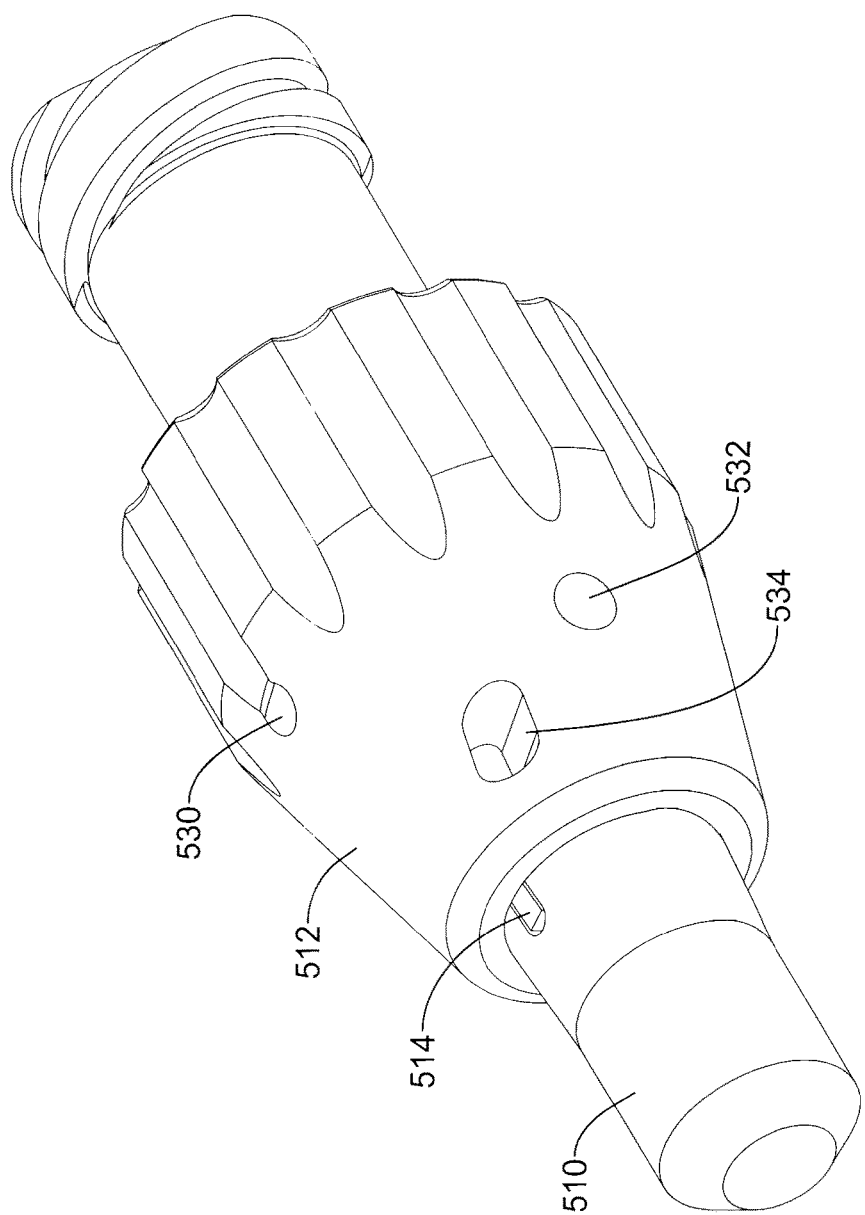
FIG. 9 is a view of the drainage catheter hub components of FIG. 7

FIGS. 7, 8 and 9 are various views of certain components of a catheter hub assembly 500. The hub assembly 500 includes a base 510, a collar 512 and a locking element 512. The base 510 includes a suture lumen 516 and may include a recess 518 for installing a sealing member (not illustrated) as described above. It may further include a slot 520 or other cavity for partially receiving the locking element 512. The base 510 may also include conventional element such as threads 526 at a proximal end 524 for connecting the hub assembly 500 to other components. It is contemplated that a catheter or other elongate member (not illustrated) extends from the distal end 522 of the base 510. An engagement element 528 on the base 510 engages with a counter element of the collar 512 as described above. The collar 512 includes a suture lumen 530 and may also include a first locking lumen 532 and a second locking lumen 534. A knurl or other gripping feature may be disposed on the collar outer surface and may be at the proximal end 540 of the collar 512. Lumen 538 extends the length of the collar 538 and includes an engagement element as described above. The locking element 514 may include a prong 542, a first arm 544 and a second arm 546. The embodiment described with respect to FIGS. 7, 8 and 9 may include and preferably does include any of the other features described in the embodiments above such as the suture, the jacket and the elongate member and in general differs only by including the locking element 514 and associated features.

Locking element 514 may be a spring made from a suitable resilient material such as, for example, stainless steel, spring steel, or a polycarbonate. It is disposed between the base 510 and the collar 512. At a high level of abstraction, locking element 514 operates to provide further positive retention of the collar 512 on the base 510. In the illustrated embodiment, this is done by capturing the locking element in a recess in the base and in a recess in the collar (slot 520 and first locking lumen 532) when the collar is in the appropriate, tightened position on the base where the engagement element and the counter element. Locking element 514 is a separate element in the illustrated embodiment, but embodiments are contemplated where the locking element might be fixed (by adhesive or otherwise) to one of the base and collar or might be integral with one of the base and collar.

In the illustrated embodiment, locking element 514 is captured between the base and the collar such that the locking element is somewhat compressed even when the engagement element and the counter element are not engaged. Thus arm 546 is firmly in slot 520 and prong 542 is against the inner surface of collar 512. This keeps the surfaces of the collar 512 and base 510 in contact and may serve to keep the collar in relative position on the base. The collar may include a first locking lumen 532 that is positioned to receive the prong 542 when the collar is locked on the base as illustrated in FIG. 8. The first locking lumen 532 may extend through the collar as illustrated to allow a user to depress the prong to allow release of the hub when desired. Alternatively, the prong may be made such that it snaps off at a pre-determined level of force to allow release of the collar. A second locking lumen 534 may also be included. This second locking lumen may receive or partially receive the prong to hold the base and the collar in relative position when the collar is not locked on the base. This second locking lumen may be in addition to or in lieu of the partial compression of the locking element described above. These features may work together to keep the collar from inadvertent or undesirable movement relative to the hub. Other locking mechanisms such as a releasable ratchet may also be incorporated into the hub.

Embodiments of the present disclosure may be used in any medical or non-medical procedure, including any medical procedure where draining visceral fluid is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What we claim is:

1. A drainage catheter, comprising:
    an elongate body member defining a central lumen and comprising a distal portion and a proximal portion, at least a portion of the elongate body member adapted for placement within a patient;
    an elongate flexible member operably connected to the distal portion of the elongate body member and extending through the lumen in at least the proximal portion of the elongate body member; and
    a hub comprising
        a base having a proximal end, a distal end, and an internal passageway, an outer surface between the proximal and distal ends, and a base side lumen extending from the internal passageway to an opening in the outer surface, wherein the outer surface includes an engagement element and a mating surface portion, and wherein the base distal end is fixed to the elongate body member proximal portion, and
        a collar having a proximal end, a distal end, an inner surface extending from the proximal end to the distal end and an outer surface extending from the proximal end to the distal end, the collar further having a collar side lumen extending from the inner surface to the outer surface, wherein the collar side lumen is positioned between the proximal and distal end of the collar, and wherein the inner surface of the collar includes a mating surface portion and a counter element,
        wherein the elongate flexible member extends through the base side lumen and the collar side lumen, and
        wherein the hub has an unlocked position where the engagement element and the counter element are not in engagement and a locked position where the engagement element and the counter element are in engagement, the collar is tightened on the base and the elongate flexible element is clamped between the mating surface portions of the base and the collar.

2. The drainage catheter of claim 1, wherein the hub further comprises an outer jacket covering the base and the collar, the outer jacket having a cavity for receiving the base and the collar.

3. The drainage catheter of claim 2, wherein the outer jacket further comprises a distal portion that tapers distally and extends distally beyond the distal ends of the base and the collar.

4. The drainage catheter of claim 1, wherein the base mating surface comprises a tapered surface that tapers at a first angle and wherein the collar mating surface comprises a tapered surface that tapers at a second angle and wherein the second angle is greater than the first angle.

5. The drainage catheter of claim 1, wherein the base mating surface is distal the engagement element disposed on the base outer surface and wherein the collar mating surface is distal the counter element disposed on the collar inner surface.

6. The drainage catheter of claim 1, wherein the base mating surface and collar mating surface are proximal to the engagement element and the counter element is distal the engagement element disposed on the base outer surface and wherein the collar mating surface is distal the counter element disposed on the collar inner surface.

7. The drainage catheter of claim 1, wherein the elongate flexible member has a first end fixed to the hub, a second end portion extending through the base side lumen and the collar side lumen, and a middle portion distal of the first end and the second end portion that is operably connected to the distal portion of the elongate body member.

8. The drainage catheter of claim 1, wherein relative proximal movement of the elongate flexible member and the hub causes the distal portion of the elongate body member to change shape.

9. The drainage catheter of claim 1, wherein relative proximal movement of the elongate flexible member and the hub causes the distal portion of the elongate body member to form a loop.

10. The drainage catheter of claim 1, wherein when the collar is tightened to the base, no relative movement between the elongate flexible member and the hub is possible and a portion of the elongate flexible member is fixed between the collar and the base.

11. The drainage catheter of claim 1, further comprising a resilient seal disposed in the base side lumen that substantially prevents fluid flow through the side lumen.

12. The drainage catheter of claim 1, further comprising a locking element disposed between the base and the collar.

13. The drainage catheter of claim 12, wherein the locking element is a spring.

14. The drainage catheter of claim 12, wherein the locking element is partially disposed in a cavity on the outer surface of the base.

15. The drainage catheter of claim 14, wherein the cavity is a slot that extends generally longitudinally.

16. The drainage catheter of claim 12, wherein the locking element is partially compressed between the collar and the base.

17. The drainage catheter of claim 12, wherein the locking element is partially compressed between the collar and the base when the engagement element and the counter element are not engaged.

18. The drainage catheter of claim 12, wherein the collar comprises a first locking cavity, the first locking cavity configured to partially receive the locking element when the collar is locked to the base.

19. The drainage catheter of claim 18, wherein the collar comprises a second locking cavity, the second locking cavity configured to partially receive the locking element when the engagement element and the counter element are not engaged.

* * * * *